(12) United States Patent
Feiweier et al.

(10) Patent No.: US 10,983,183 B2
(45) Date of Patent: Apr. 20, 2021

(54) METHOD AND APPARATUS FOR DETERMINATION OF PHASE DISTRIBUTIONS IN MAGNETIC RESONANCE IMAGING

(71) Applicant: Siemens Healthcare GmbH, Erlangen (DE)

(72) Inventors: Thorsten Feiweier, Poxdorf (DE); Daniel Niederloehner, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 142 days.

(21) Appl. No.: 16/042,324

(22) Filed: Jul. 23, 2018

(65) Prior Publication Data
US 2019/0025386 A1    Jan. 24, 2019

(30) Foreign Application Priority Data
Jul. 24, 2017 (EP) ..................... 17182768

(51) Int. Cl.
*G01R 33/24* (2006.01)
*G01R 33/565* (2006.01)
(Continued)

(52) U.S. Cl.
CPC ............ *G01R 33/246* (2013.01); *A61B 5/055* (2013.01); *G01R 33/4804* (2013.01);
(Continued)

(58) Field of Classification Search
CPC ............ G01R 33/246; G01R 33/56316; G01R 33/4804; G01R 33/56563; G01R 33/243;
(Continued)

(56) References Cited

U.S. PATENT DOCUMENTS 5,162,737 A     11/1992  Nozokido et al.
6,630,827 B1 *  10/2003  Miyoshi ............... G01R 33/565
                                            324/307
(Continued)

FOREIGN PATENT DOCUMENTS

WO    WO-2016116545 A1 *   7/2016   ............. A61B 5/055

OTHER PUBLICATIONS

Borrello et al, "Chemical Shift-based True Water and Fat Images: Regional Phase Correction of Modified Spin-Echo MR Images" Radiology, Radiological Society of North America, vol. 164, No. 2, pp. 531-537,(1987).
(Continued)

*Primary Examiner* — Tung X Nguyen
*Assistant Examiner* — Feba Pothen
(74) *Attorney, Agent, or Firm* — Schiff Hardin LLP

(57) ABSTRACT

In a method and apparatus for determination of phase distributions in MR imaging, a measured phase distribution of the region of interest is combined with at least one second phase value to form a combination-phase distribution, wherein the phase values of the combination-phase distribution are restricted to a defined presentation interval. A correction-phase distribution is generated, based on a known magnetic field distribution in the region of interest. The phase values thereof are not restricted to the defined presentation interval. A corrected combination-phase distribution is generated using the correction-phase distribution and the combination-phase distribution, in which the phase values are restricted to the defined presentation interval. An absolute combination-phase distribution is generated from the corrected combination-phase distribution, in which the phase values are not restricted to the defined presentation interval.

9 Claims, 8 Drawing Sheets

(51) Int. Cl.
    *A61B 5/055*     (2006.01)
    *G01R 33/48*     (2006.01)
    *G01R 33/563*     (2006.01)
    *A61B 5/00*     (2006.01)
    *G01R 33/3415*     (2006.01)

(52) U.S. Cl.
    CPC . *G01R 33/56316* (2013.01); *G01R 33/56563* (2013.01); *A61B 5/0037* (2013.01); *G01R 33/243* (2013.01); *G01R 33/3415* (2013.01); *G01R 33/56536* (2013.01)

(58) Field of Classification Search
    CPC .......... G01R 33/3415; G01R 33/56536; A61B 5/055; A61B 5/0037
    See application file for complete search history.

(56) References Cited

U.S. PATENT DOCUMENTS

| | | | |
|---|---|---|---|
| 9,983,284 B2 | 5/2018 | Eggers et al. | |
| 2015/0355306 A1* | 12/2015 | Stemmer | G01R 33/543 |
| | | | 324/309 |
| 2017/0038446 A1* | 2/2017 | Liu | A61B 5/4872 |

OTHER PUBLICATIONS

Yang, "Computing Magnetic Susceptibility Maps from Gradient Recalled Echo MRI for use in Multiple Sclerosis Studies" A Thesis; The Ohio State university, Columbus, Ohio, (2013).

* cited by examiner $B_M + B_P$

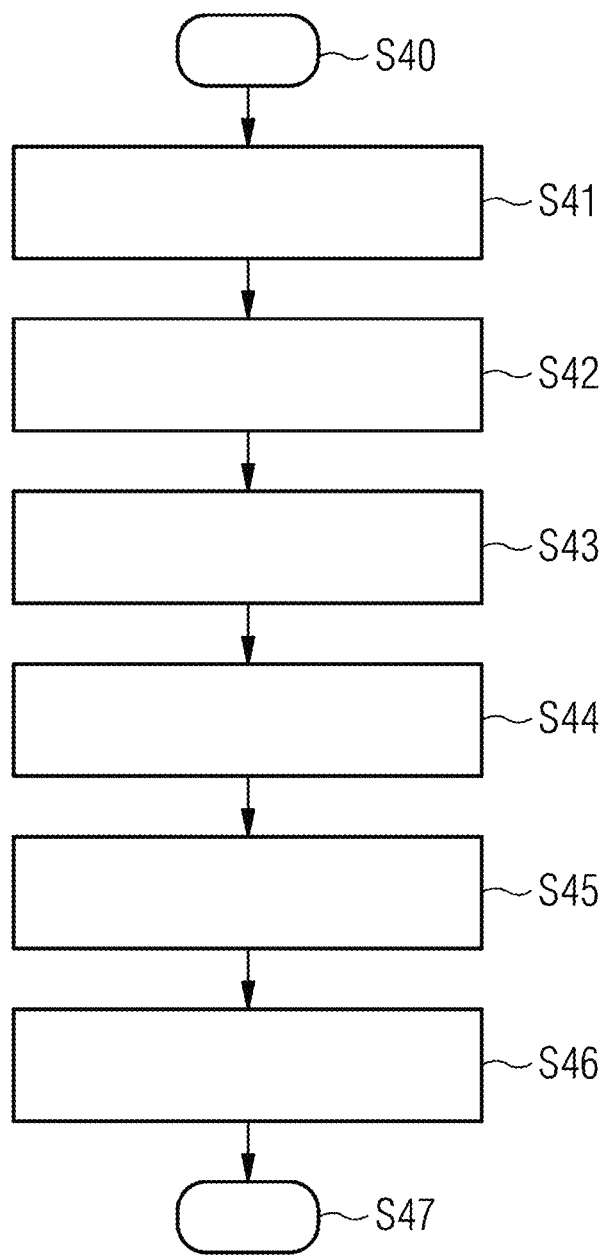

METHOD AND APPARATUS FOR DETERMINATION OF PHASE DISTRIBUTIONS IN MAGNETIC RESONANCE IMAGING

BACKGROUND OF THE INVENTION

Field of the Invention

The present invention concerns the determination of phase distributions in magnetic resonance (MR) imaging and in particular a method for the determination of a phase distribution of a region of interest, which is determined in order to generate an MR image of the region of interest by operation of an MR system.

Description of the Prior Art

A number of MR imaging methods use—sometimes in addition to the amplitude—the phase of the MR signal as basic information. Such MR imaging methods include, for example, B0 mapping, which includes spatial representation of a variation of the B0 field amplitude, susceptibility-weighted imaging (SWI), which is based on image weighting taking into account tissue-induced variations in the local B0 field amplitude (for example, due to the presence of hemoglobin in the event of hemorrhage), quantitative susceptibility mapping (QSM), which includes quantitative spatial determination and representation of local, dipole-like B0 field distortions (for example due to the presence of iron, calcium or suitable contrast agents), the Dixon method, which enables a separate representation of the spatial distribution of signal components of, for example, fat- and water-bound nuclei of hydrogen, thermometry with which spatial temperature distribution is determined, and elastography for the determination of the spatial distribution of mechanical tissue parameters.

An essential step with these imaging methods is the ascertainment of the spatial distribution of a phase difference relative to a previously determined or defined reference phase, i.e. a spatial phase-difference distribution. This phase-difference distribution then represents the basis for further processing steps. A problem with such methods is due to the limited value range of the phase information ascertained from measured variables. The value range of phases or phase differences is restricted to the interval $[-\pi; +\pi]$.

The "actual", i.e. absolute phase difference from a reference value is determined using special method steps, which generally make assumptions regarding the spatial development of the signal phase. For example, one assumption may be that the signal phase only changes slightly between adjacent image points. Due to the design of the basic field magnet, strong spatial variations in the signal phase are unavoidable in particular at the edge of the image recording region. In these regions, errors frequently occur in the determination of the actual phase difference which consequently result in erroneous or imprecise representations.

The prior art frequently uses "phase-unwrapping" techniques in order—based on a reference phase—to ascertain the actual phase difference. Herein, generally a slow spatial variation of the phase is assumed. If the phase difference of an adjacent image point exceeds a defined threshold value, for example $+\pi$ or $-\pi$, this adjacent point is assigned an additional phase, for example $+2\pi$ or $-2\pi$. Thus, the successive consideration of further adjacent points gradually establishes a phase map, i.e. phase distribution, with a value range that is no longer restricted to the interval $[-\pi; +\pi]$.

However, in the edge region of the magnet, the component of the signal phase induced by inhomogeneities of the magnetic field can vary very rapidly thus resulting in the determination of erroneous additional phases. The successive approach used causes these errors to be propagated over large image regions.

A further known approach is to use filter techniques, wherein a spatial high-pass filter suppresses slow spatial variations in phase and so the high-frequency components are extracted as a "useful signal". However, in the edge region of the magnet, the components of the signal phase induced by inhomogeneities in the magnetic field vary very rapidly and are hence erroneously assigned to the useful signal.

There is therefore a need for an improved method for the determination of phase distributions in MR imaging methods based on phase information, which improves the robustness and precision of the MR methods in the region of rapid spatial phase variations, in particular at the edge of image recording regions.

SUMMARY OF THE INVENTION

According to a first aspect of the invention, a method is provided for the determination of a phase distribution of a region of interest by means of an MR system. A phase distribution is determined within the region of interest in order to generate an MR image, wherein a known magnetic field distribution in the region of interest is taken into account. In a first step, a phase distribution measured within the region of interest is provided. In a further step, at least one second phase value is provided. In an additional step, the first measured phase distribution and the at least one second phase value are combined with one another in order to generate a combination-phase distribution. The phase values of the combination-phase distribution are restricted to a defined presentation interval. In an additional step, a correction-phase distribution is generated, which is based on the known magnetic field distribution in the region of interest, wherein the phase values of the correction-phase distribution are not restricted to the defined presentation interval. In a further step, a corrected combination-phase distribution is generated using the correction-phase distribution and the combination-phase distribution. The correction-phase distribution can be subtracted, in other words separated or subtracted, from the combination-phase distribution in order to generate a corrected combination-phase distribution. For example, it is also possible to perform complex-conjugate multiplication or use another mathematical method to take account of the correction-phase distribution and the combination-phase distribution. The phase values of the corrected combination-phase distribution are restricted to the defined presentation interval. In yet a further step, an absolute combination-phase distribution is generated from the corrected combination-phase distribution, wherein the phase values of the absolute combination-phase distribution are not restricted to the defined presentation interval.

The corrected combination-phase distribution is then used to process MR data acquired according to one or more of the aforementioned MR imaging methods that make use of the spatial distribution of a phase difference relative to a previously determined or defined reference phase for processing of such MR data.

The method according to the invention utilizes knowledge of the spatial distribution of a basic magnetic field, in particular of rapidly spatially varying contributions of a known magnetic field distribution in an edge region of a region of interest and thus reduces the errors in the determination of phase distributions in the edge region. In particular, the method according to the invention reduces the spatial variation of a signal phase of measured MR data by separating a component of a priori known spatial variations in the signal phase. This generates a more benign spatial phase distribution, which is substantially induced by an object, which enables less error-susceptible determination of relative phase relationships in MR imaging methods based on phase information. Hence, this results in improved robustness and precision of MR imaging methods based on phase information, in particular in the edge of image recording regions.

The method can additionally include the generation of a corrected absolute combination-phase distribution using the correction-phase distribution and the absolute combination-phase distribution. The method can include the addition of the correction-phase distribution to the absolute combination-phase distribution.

The correction-phase distribution $\varphi_{korr}$ can be determined in accordance with the formula $$\varphi_{korr}(r)=\gamma \Delta B_0(r) T_{eff},$$

wherein $\gamma$ is the gyromagnetic ratio, $\Delta B_0(r)$ is a magnetic field distribution in the region of interest, r is the position vector in the region of interest, and $T_{eff}$ is an effective evolution time. The above formula enables the correction-phase distribution to be determined simply and rapidly based on the magnetic field distribution and the effective evolution time.

The generation of the absolute combination-phase distribution can be performed based on a phase-unwrapping technique. A phase-unwrapping technique known in the prior art is an efficient way of generating an absolute phase distribution with phase values, which are not restricted to a defined presentation interval.

The combination of the first measured phase distribution and the at least one second phase value can be a determination of a phase-difference distribution. The phase-difference distribution is a spatial assignment of phase differences of individual voxels in the region of interest. This enables a quick and efficient determination of phase differences in MR imaging methods for the generation of MR images.

The determination of the first measured phase distribution can include measurement of a phase distribution of the region of interest, i.e. a spatial distribution of phase values, or in other words a spatial assignment of phase values to individual points in the region of interest, after a first evolution period. Herein, the phase values of the phase distribution are based on the known magnetic field distribution in the region of interest. The determination of a phase distribution based on a magnetic field distribution in the region of interest following a first evolution period is required in numerous MR imaging methods for the generation of MR images and hence phase combination can be performed quickly and efficiently.

The provision of at least one second phase value can be a provision of a second measured phase distribution of the region of interest. Furthermore, the provision of the second measured phase distribution can be a measurement of a phase distribution of an MR image after a second evolution period that is different from the first evolution period. The provision of at least one second phase value can be a definition of a global phase value of the region of interest. Hence, a phase distribution can be determined quickly and efficiently in many MR imaging methods for the generation of MR images.

According to a further aspect, an MR system is provided for the determination of a phase distribution of a region of interest. The MR system has an MR data acquisition scanner operated by a control computer. The MR system has a memory in which control information is stored that can be executed by the control computer. The MR system is designed to implement the above-described method according to the invention when the control information (code) is executed in the control computer.

Technical effects are achieved such an MR system for the determination of a phase distribution of a region of interest that are comparable with the technical effects described above for the method according to the invention.

The present invention also encompasses a non-transitory, computer-readable data storage medium encoded with programming instructions that, when the storage medium is loaded into a computer or computer system of a magnetic resonance imaging apparatus, cause the computer or computer system to operate the magnetic resonance imaging apparatus in order to implement any or all of the embodiments of the method according to the invention, as described above.

The above-described features and the features described below can be used not only in the explicitly described combinations, but also in further combinations or in isolation without departing from the scope of the present invention.

BRIEF DESCRIPTION OF THE DRAWINGS

FIG. 2b shows a line graph of the magnetic field distribution shown in FIG. 2a along a central line of the two-dimensional representation in FIG. 2a.

FIG. 3b shows a line graph of the magnetic field distribution shown in FIG. 3a along a central line of the two-dimensional representation in FIG. 3a.

FIG. 4a shows a two-dimensional representation of a superimposition of the magnetic field distributions $B_0 = B_M + B_P$ in FIGS. 2a and 3a.

FIG. 4b shows a line graph of the magnetic field distribution shown in FIG. 4a along a central line of the two-dimensional representation in FIG. 4a.

FIG. 5b shows a line graph of the phase-difference distribution $\Delta\varphi(r)$ shown in FIG. 5a along a central line of the two-dimensional representation in FIG. 5a.

FIG. 6b shows a line graph of the corrected phase-difference distribution of the region of interest shown in FIG. 6a along a central line of the two-dimensional representation in FIG. 6a.

FIG. 9 is a flowchart with steps for carrying out the method for the determination of a phase distribution of a region of interest according to an exemplary embodiment of the invention.

DESCRIPTION OF THE PREFERRED EMBODIMENTS

Figure 1:
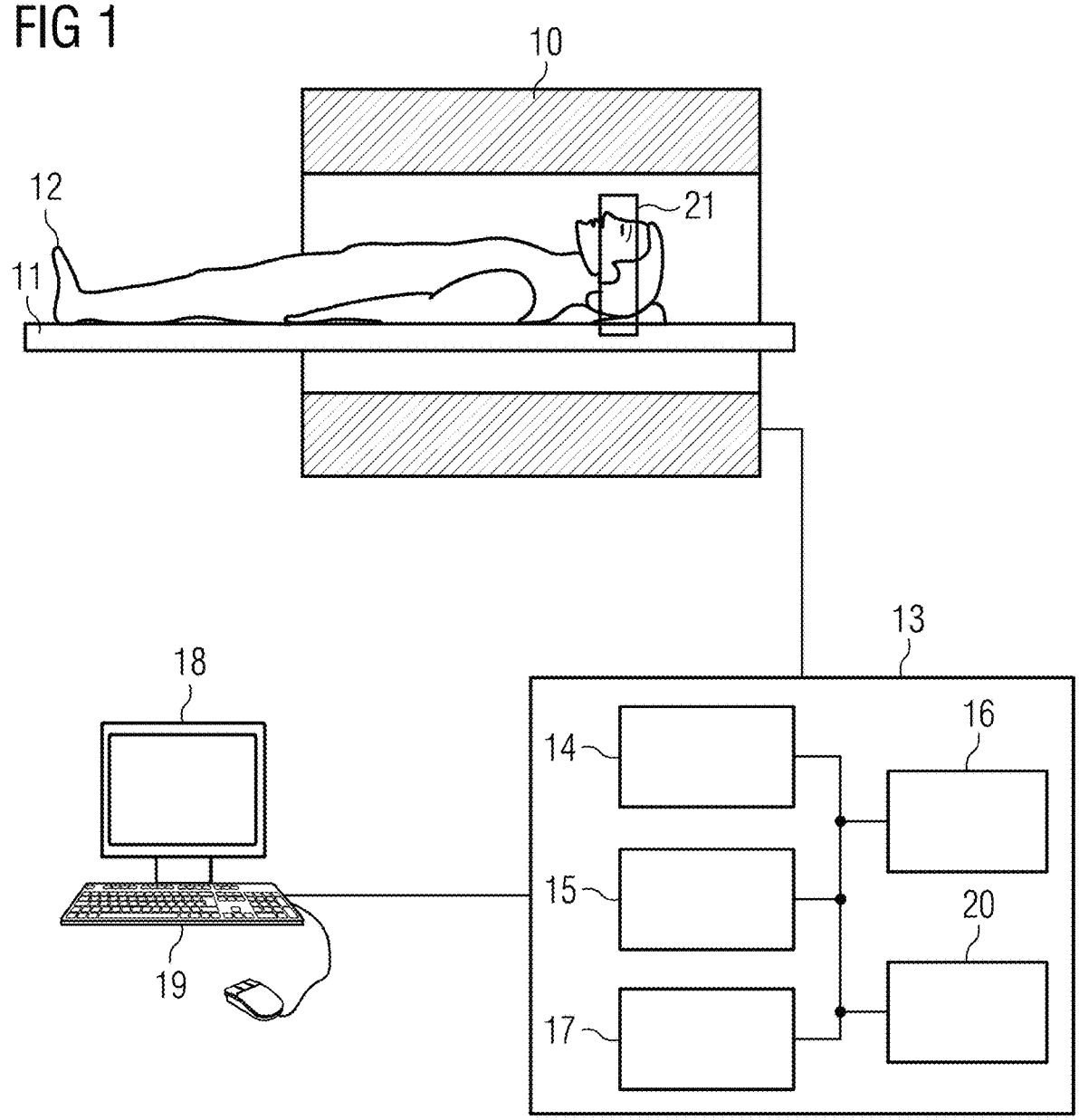
FIG. 1 schematically illustrates an MR system with which the method for the determination of a phase distribution of a region of interest can be carried out according to the invention.

FIG. 1 schematically shows an MR system with which the method for the determination of a phase distribution of a region of interest 21 according to the invention can be carried out.

A person 12 under examination, or more generally an object under examination, is in moved into the tunnel of the system, wherein a region of interest 21 is examined by the MR system. The magnetic resonance system has a scanner 10 with a basic field magnet that generates a basic magnetic field B0. The person 12 under examination, arranged on a bed 11, is moved into the center of the scanner 10 in order to record spatially encoded magnetic signals from the region of interest 21. Radiation of radio-frequency (RF) pulse sequences and switching of magnetic field gradients causes certain nuclear spins in the person 12 to be deflected from the magnetization generated by the basic field B0, out of the equilibrium position. Currents induced in RF reception coils, as the excited spins return to the equilibrium position, are detected as magnetic resonance signals, which are then transformed into image data. The general mode of operation for creating MR images and the detection of magnetic resonance signals are known to those skilled in the art, so a more detailed description is not necessary herein.

The magnetic resonance system further has a control computer 13 that controls the MR scanner 10. The central control computer 13 is designed to implement the method described below for the determination of a phase distribution of a region of interest 21, and includes a gradient controller 14 that controls switching the magnetic field gradients, and an RF controller 15 that controls radiating the RF pulses for deflecting the nuclear spins from the equilibrium position. A memory 16 stores the imaging sequences required for recording the MR images and all programs required for the operation of the MR system. A recording controller 17 controls the image recording and hence, dependent on the chosen imaging sequences, the sequence of the magnetic field gradients and RF pulses and the receiving intervals of MR signals. Thus, the recording controller 17 also controls the gradient controller 14 and the RF controller 15. In a computing processor 20, MR images are calculated (reconstructed) and visualized on a display 18. An operator can operate the MR system via an input unit 19 of the MR system. The memory 16 can have imaging sequences and program modules, which carry out the method according to the invention when one of the modules shown is executed in the computing processor 20. The memory 16 thus stores control information (code) that can be executed by the control computer 13. The recording controller 17 is also designed such that it is able to assist in the method described below for the determination of a phase distribution of the region of interest 21.

According to the invention, the MR system in FIG. 1 is designed such that, when the control information is executed in the MR control computer 13, it determines at least one phase distribution of the region of interest 21 in order to generate an MR image of the region of interest 21 and, for the generation of an absolute phase combination distribution, the phase values thereof are not restricted to a defined presentation interval and take account of a known magnetic field distribution in the region of interest 21.

The basis of the method according to the invention is the separation of magnetically induced phase differences, in particular phase differences induced by fixed components (e.g. RF whole body coil, covering, gradient coil, etc.) with known magnetic field distributions and phase differences induced by non-fixed components (e.g. patient bench, RF local coils, positioning aids) with known positions and magnetic field distributions. The magnetically induced phase difference can be derived from a known spatial magnetic field distribution $B_M(r)$, which is, for example, determined on the installation of the MR system, during regular service procedures or even before delivery as a "design" parameter. The spatial distribution of the desired signal-phase difference $\Delta\varphi(r)=\varphi(r)-\varphi_{ref}$ can be derived from the complex MR signal with amplitude A at the location r:

$$S(r)=A(r)\exp(i\varphi(r))$$

Wherein the following relationship also applies:

$$\varphi(r)=\Delta\omega_0(r)T_{eff}+\varphi_{acq}(r)+\varphi_{coil}(r)=\gamma\Delta B_0(r)T_{eff}+\varphi_{acq}(r)+\varphi_{coil}(r)$$

Here $\Delta\omega_0$ (r) designates the deviation of the local precession frequency from a reference value (generally the current center frequency of the RF receiving system), $\gamma$ the gyromagnetic ratio and $T_{eff}$ an effective evolution time that is dependent upon the measurement. For a gradient echo measurement, $T_{eff}=TE$ applies, for example, wherein the echo time TE defines the time interval between an RF excitation pulse and the time of data recording. At this point, the local field deviation $\Delta B_0(r)$ contains the magnetic field distribution $\Delta B_M(r)$ and object-induced magnetic field variations $\Delta B_F(r)$, but also further influencing variables such as the effective change in the precession frequency due to chemical displacement $\Delta B_{CS}(r)$. For example, in the case of MR elastography, the signal can be impressed in a targeted manner with a phase term $\varphi_{acq}(r)$ independent of $T_{eff}$ and which provides the desired phase contrast. Local coils and RF transmission effects can cause an additional phase term $\varphi_{coil}(r)$ to occur, which can be determined and taken into account by reference measurements.

Particularly at the edge of the imaging region, the signal phase $\Delta\varphi(r)$ has rapid spatial variations as a result of the contribution $\gamma\Delta B_M(r)T_{eff}$. The method according to the invention now provides for the precise separation of this known contribution before the use of "phase-unwrapping" methods or filter techniques. Hence, the latter work on a "benign" (less strongly spatially fluctuating)

$$\varphi_{eff}(r)=\varphi(r)-\gamma B_M(r)T_{eff}.$$

This enables the ascertainment of the sought-for spatial parameter distributions with improved robustness or precision. If necessary—for example for the determination of B0 maps—the separated magnetic component can be re-added to the phase difference at the end of the calculation. Since the magnetic field is known as an absolute value, this can take place without restriction of the value range of the phase.

The reference phase $\varphi_{ref}$ can be defined arbitrarily or determined by the phase at a position in the image (or a mean over a defined range). The reference phase may also relate to a further measurement with changed settings. For the ascertainment of B0 maps, it is, for example, possible to perform two measurements with different effective evolution times $T_{eff,1}$ and $T_{eff,2}$. The signal phase difference is then obtained as $\Delta\varphi(r)=\varphi_1(r)-\varphi_2(r)$, wherein the following relationships apply:

$$S_1(r) = A_1(r)\exp(i\varphi_1(r)),$$

$$S_2(r) = A_2(r)\exp(i\varphi_2(r)),$$

$$\varphi_1(r) = \Delta\omega_0(r)T_{eff,1} + \varphi_{acq,1}(r) + \varphi_{coil,1}(r)$$
$$= \gamma\Delta B_0(r)T_{eff,1} + \varphi_{acq,1}(r) + \varphi_{coil,1}(r),$$

$$\varphi_2(r) = \Delta\omega_0(r)T_{eff,2} + \varphi_{acq,2}(r) + \varphi_{coil,2}(r)$$
$$= \gamma\Delta B_0(r)T_{eff,2} + \varphi_{acq,2}(r) + \varphi_{coil,2}(r).$$

If the two measurements are performed with an identical coil configuration $\varphi_{coil,1}(r)=\varphi_{coil,2}(r)$ and, apart from the evolution time, an identical course $\varphi_{acq,1}(r)=\varphi_{acq,2}(r)$, the sought-for signal-phase difference is obtained from the formula $$\Delta\varphi(r)=\gamma\Delta B_0(r)(T_{eff,1}-T_{eff,2}).$$

Here once again, the known, rapidly spatially varying contribution due to the basic magnetic field can be separated by means of the formula $$\Delta\varphi_{eff}(r)=\gamma\Delta B_0(r)(T_{eff,1}-T_{eff,2})-\gamma\Delta B_M(r)(T_{eff,1}-T_{eff,2}),$$

and thus a "more benign" spatial phase distribution is obtained for the further data processing.

To summarize, the method according to the invention reduces the spatial variation of a signal phase thus permitting a more robust and more precise determination of relative phase relationships in the image.

As an example, the method is described for recording absolute B0 maps. The aim of recording B0 maps is to determine $\Delta B_0(r)=\Delta B_M(r)+\Delta B_P(r)$, wherein, for purposes of simplicity, no further influencing variables (e.g. $\Delta B_{SC}(r)$) are taken into account. To this end, at least two measurements with different effective evolution times $T_{eff,1}$ and $T_{eff,2}$ are recorded and the spatial distribution of the relative signal phases is determined by the formula $$\Delta\varphi(r)=\gamma\Delta B_0(r)(T_{eff,1}-T_{eff,2})=\gamma(\Delta B_M(r)+\Delta B_P(r))(T_{eff,1}-T_{eff,2}).$$

In the prior art, the desired B0 information would be determined from the following relationship:

$$\Delta B_0(r)=\Delta\varphi(r)/(\gamma(T_{eff,1}-T_{eff,2})).$$

Since the phase difference only has a value range of $-\pi$ and $+\pi$, the directly accessible value range for the field map is restricted to $+-\pi/(\gamma(T_{eff,1}-T_{eff,2}))$. For example, measuring with $T_{eff,1}=4.8$ ms and $T_{eff,2}=9.6$ ms produces a value range of about $+/-2.4$ µT. With a basic field strength of 1.5 T, this corresponds to a relative field change of $+/-1.6$ ppm. At the edge of the imaging region, the inhomogeneities of the basic field magnet can very possibly be a few tens of ppm. As a result, this order of magnitude can no longer be depicted directly with the measurement, so unique determination of the B0 amplitude is not directly possible.

The following two-dimensional example assumes a magnetically induced field distribution according to a spherical harmonic function of the type $\Delta B_M(x, y)=B_{M,0}*\cos(5*\alpha)*(r/r_0)^5$, wherein $\alpha$ is the angle in the plane, r is the distance to the center, $r_0$ is a reference radius and $B_{M,0}$ is a scaling factor. This is superimposed with an object-induced field distribution according to a quadratic function $\Delta B_P(x, y)= B_{P,0}*(r/r_0)^2$.

The actual physical fields have the following forms, wherein the units used for representation were selected arbitrarily and are identical in all the figures.

Figure 2A:
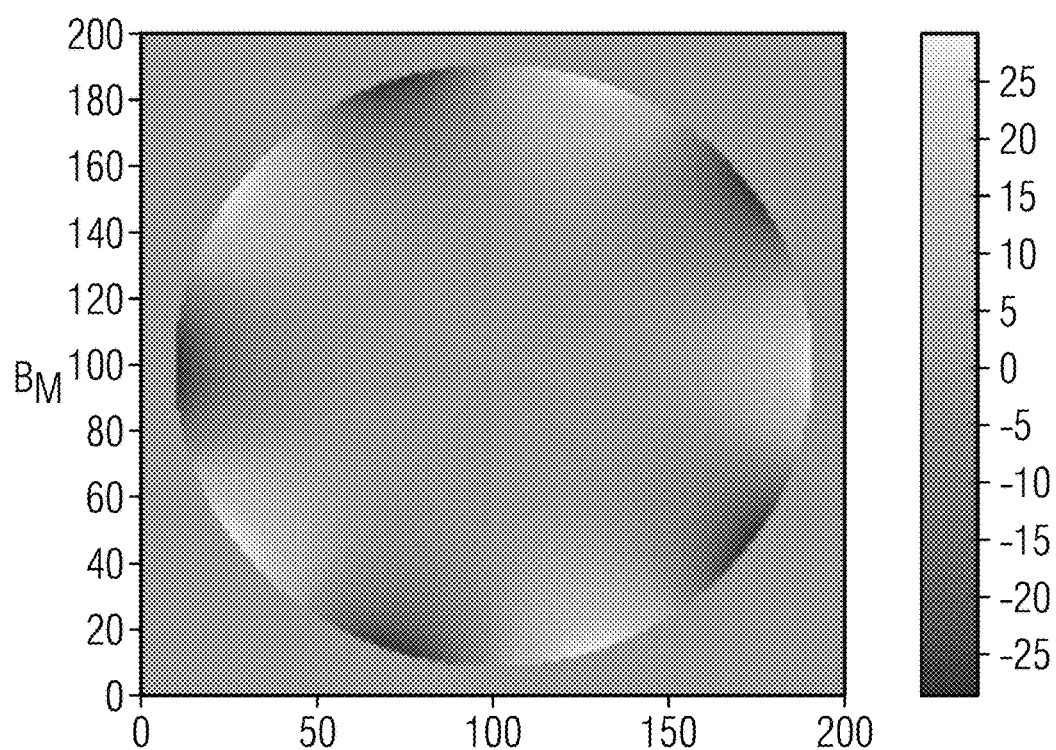
FIG. 2a shows a two-dimensional representation of a magnetic field distribution $B_M$ in a region of interest, which is based on system-specific circumstances of the MR system.

FIG. 2a shows a two-dimensional representation of a magnetic field distribution $B_M$ in a region of interest, which is based on system-specific circumstances of the MR system, such as, for example, the design of the basic field magnet. The edge regions of the circular representation of the magnetic field distribution $B_M$ shown have strong spatial variation with a high spatial frequency of the magnetic field strength.

Figure 2B:
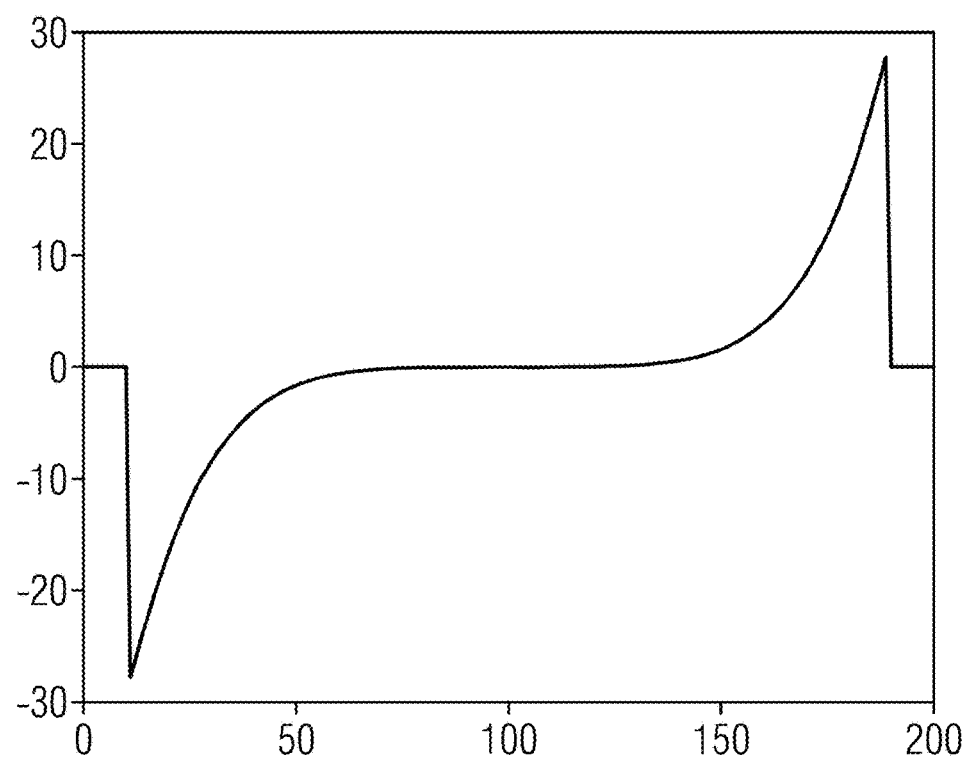

FIG. 2b shows a line graph of the magnetic field distribution shown in FIG. 2a along a central line of the two-dimensional representation in FIG. 2a.

Figure 3A:
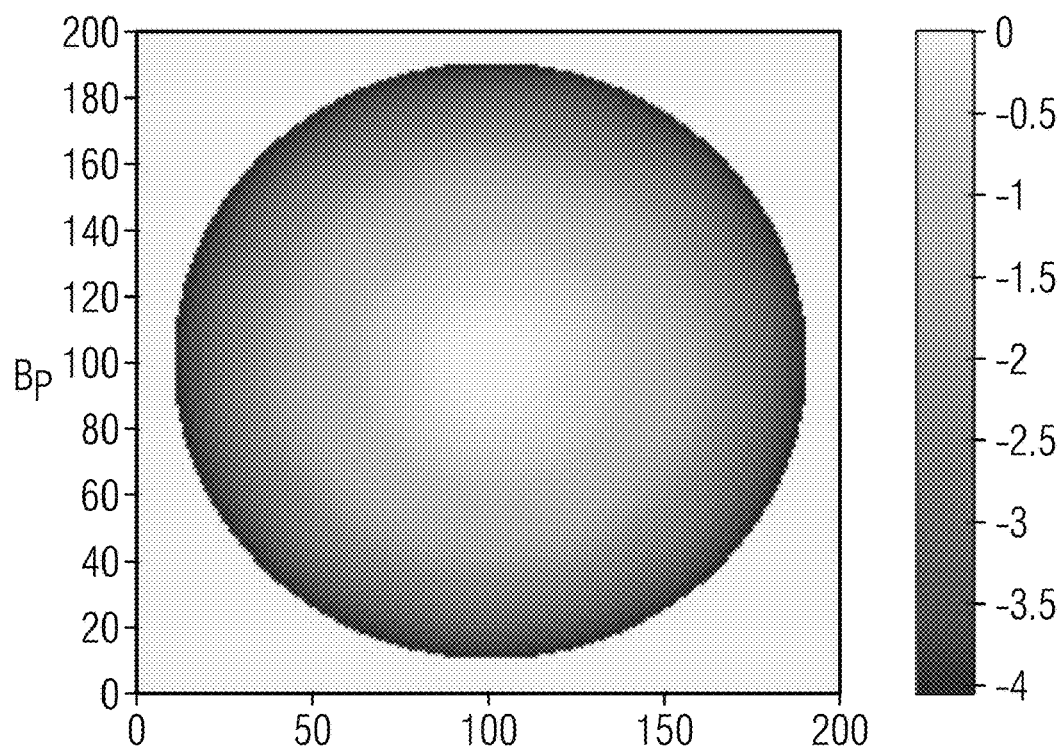
FIG. 3a shows a two-dimensional representation of a magnetic field distribution $B_P$ induced by an object in the region of interest.

FIG. 3a shows a two-dimensional representation of a magnetic field distribution $B_P$ induced by an object in a region of interest. The edge regions of the circular representation of the magnetic field distribution $B_P$ shown have uniform magnetic field strength.

Figure 3B:
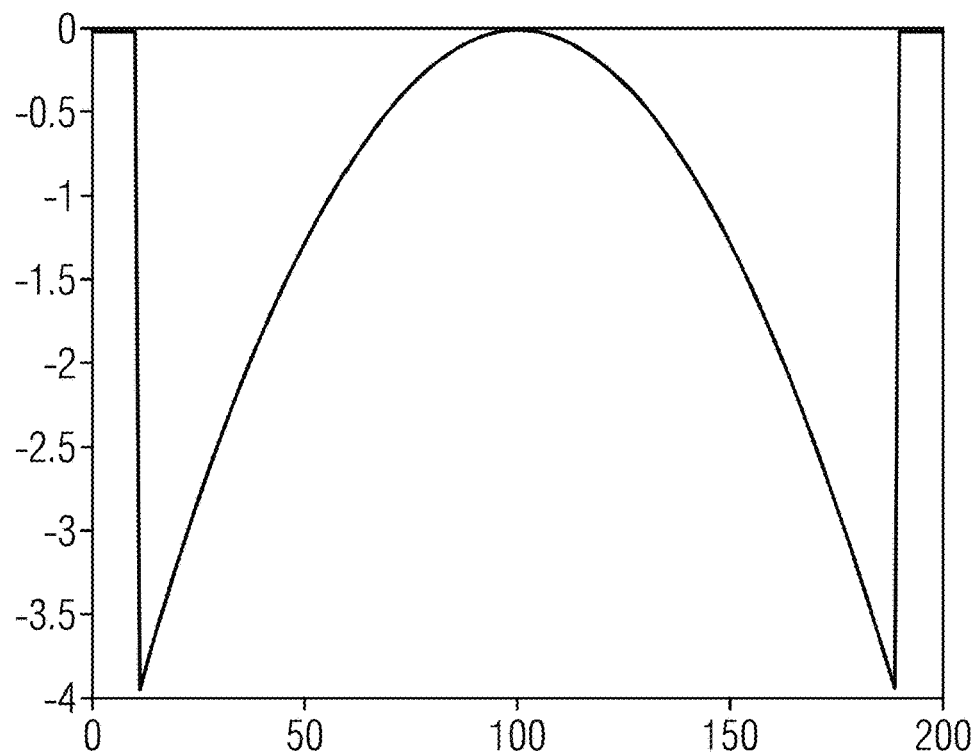

FIG. 3b shows a line graph of the magnetic field distribution shown in FIG. 3a along a central line of the two-dimensional representation in FIG. 3a.

Figure 4A:
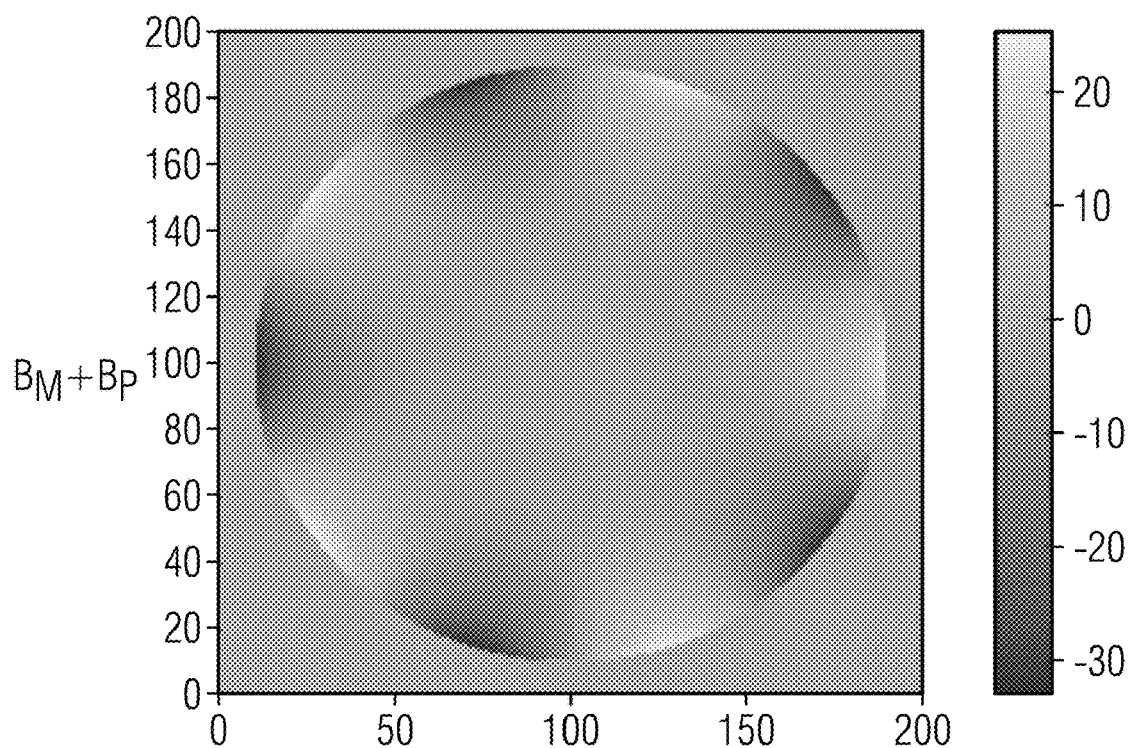

FIG. 4a shows a two-dimensional representation of a superimposition of the magnetic field distributions $B_0=B_M+B_P$ in FIGS. 2a and 3a. In the superimposed magnetic field distribution $B_0=B_M+B_P$, the influence of the magnetic field distribution $B_M$ predominates so that the edge regions of the circular representation also have strong spatial variation with a high spatial frequency of the magnetic field strength.

Figure 4B:
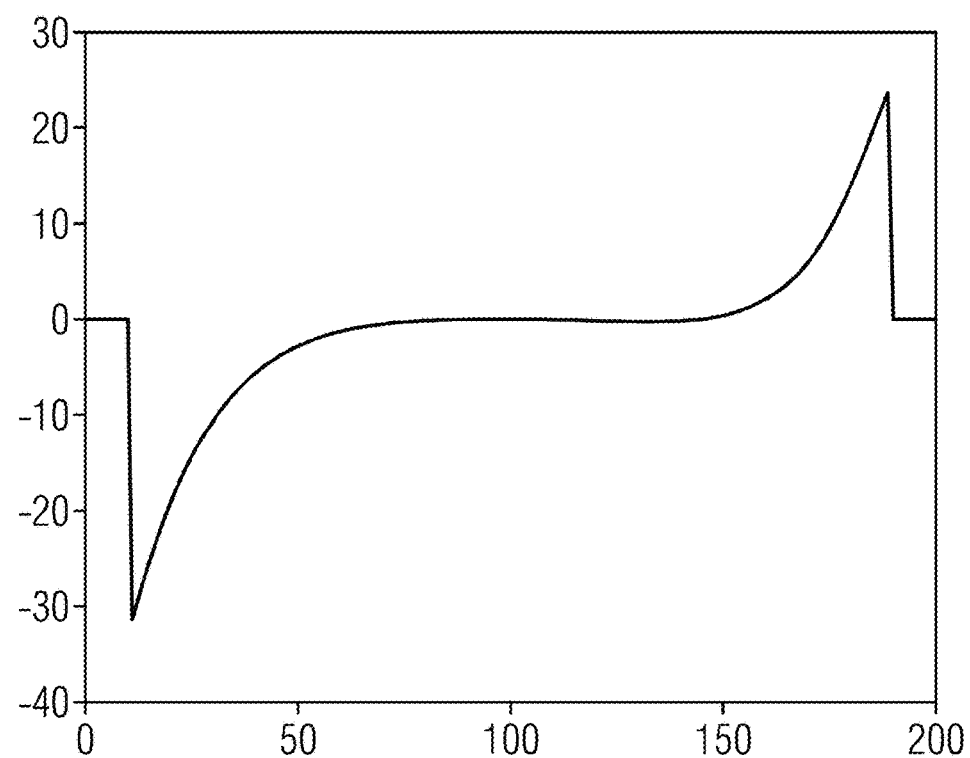

FIG. 4b shows a line graph of the magnetic field distribution shown in FIG. 4a along a central line of the two-dimensional representation in FIG. 4a.

A measurement of phase distribution by the MR system can only detect the superimposed field distribution $\Delta B_0(x, y)$ via the determination of a phase difference $\Delta\varphi(r)$ and supplies data with a restricted value range.

Figure 5A:
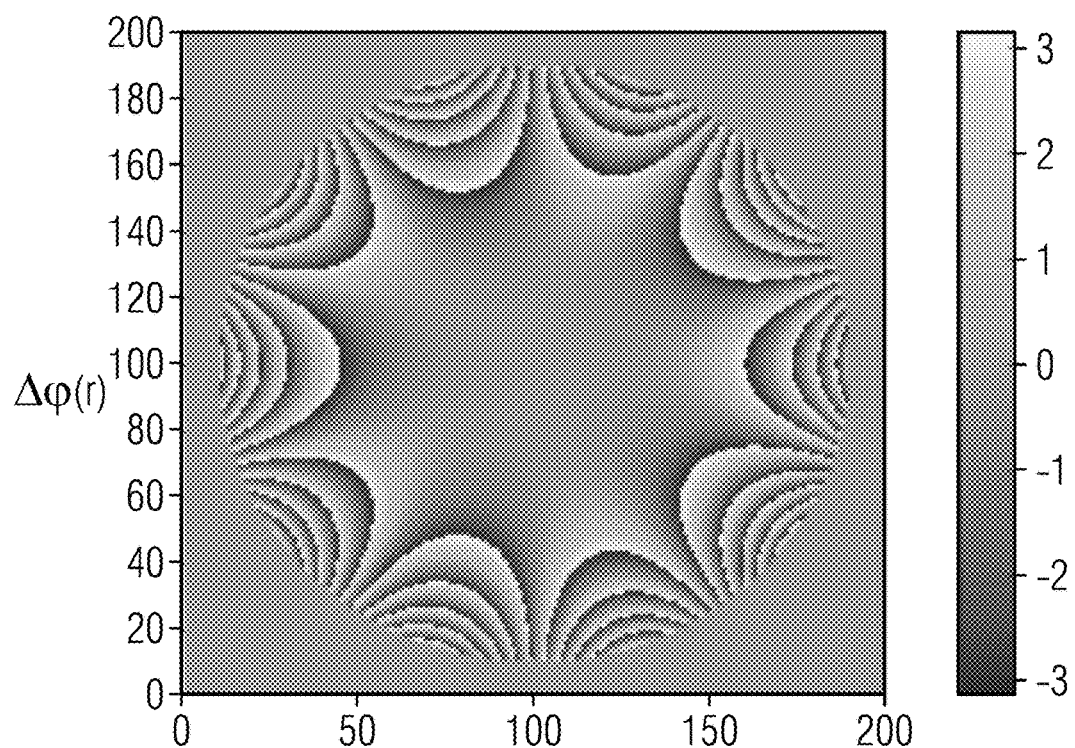
FIG. 5a shows a two-dimensional representation of a phase-difference distribution $\Delta\varphi(r)$ of the region of interest, which is based on the magnetic field distribution shown in FIGS. 4a and 4b and wherein the phase values thereof are restricted to the interval $[-\pi; +\pi]$.

Therefore, evaluation routines "see" the following spatial phase distribution, which is depicted in FIG. 5a.

FIG. 5a shows a two-dimensional representation of a phase-difference distribution $\Delta\varphi(r)$ of the region of interest, which is based on the magnetic field distribution shown in FIGS. 4a and 4b and wherein the phase values thereof are restricted to the interval $[-\pi; +\pi]$.

Figure 5B:
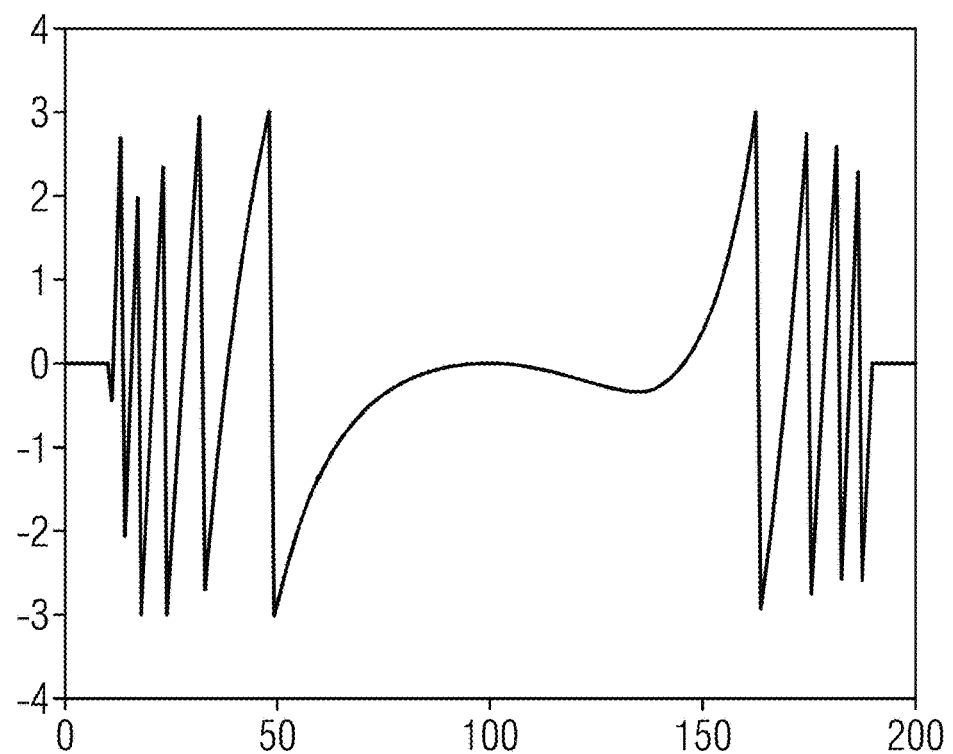

FIG. 5b shows a line graph of the phase-difference distribution $\Delta\varphi(r)$ shown in FIG. 5a along a central line of the two-dimensional representation in FIG. 5a.

A number of phase jumps can be identified in the edge regions of the corrected phase-difference distribution in FIGS. 5a and 5b. These phase jumps are caused by the restriction of the phase values to the interval $[-\pi; +\pi]$.

The problem of the ambiguous values in the edge region is clearly identifiable. In the prior art, these rapid spatial variations had to be detected by means of suitable image processing methods (e.g. "phase-unwrapping") and assigned correctly and—in particular in the case of noisy data—this can result in errors.

According to the invention, first, the known contribution $\Delta\varphi_M(r)=\gamma B_M(r)(T_{eff,1}-T_{eff,2})$ of the magnet is separated from the determined phase difference $\Delta\varphi(r)$. Herein, the magnetically induced phase is restricted to the value range between $-\pi$ and $+\pi$. This achieves a more benign spatial phase distribution, which is substantially object-induced, as shown in FIG. 6.

Figure 6A:
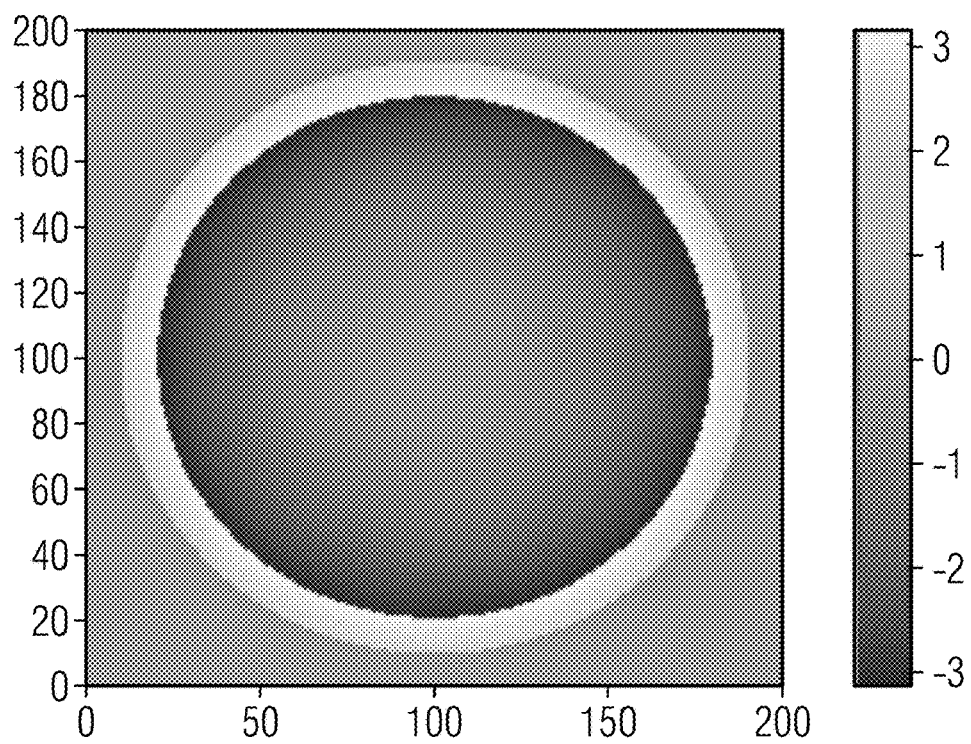
FIG. 6a shows a two-dimensional representation of a corrected phase-difference distribution of the region of interest, which is based on the phase-difference distribution shown in FIG. 5a and wherein the phase values thereof are restricted to the interval $[-\pi; +\pi]$.

FIG. 6a shows a two-dimensional representation of a corrected phase-difference distribution of the region of interest, which is based on the phase-difference distribution shown in FIG. 5a and wherein the phase values thereof are restricted to the interval $[-\pi; +\pi]$.

Figure 6B:
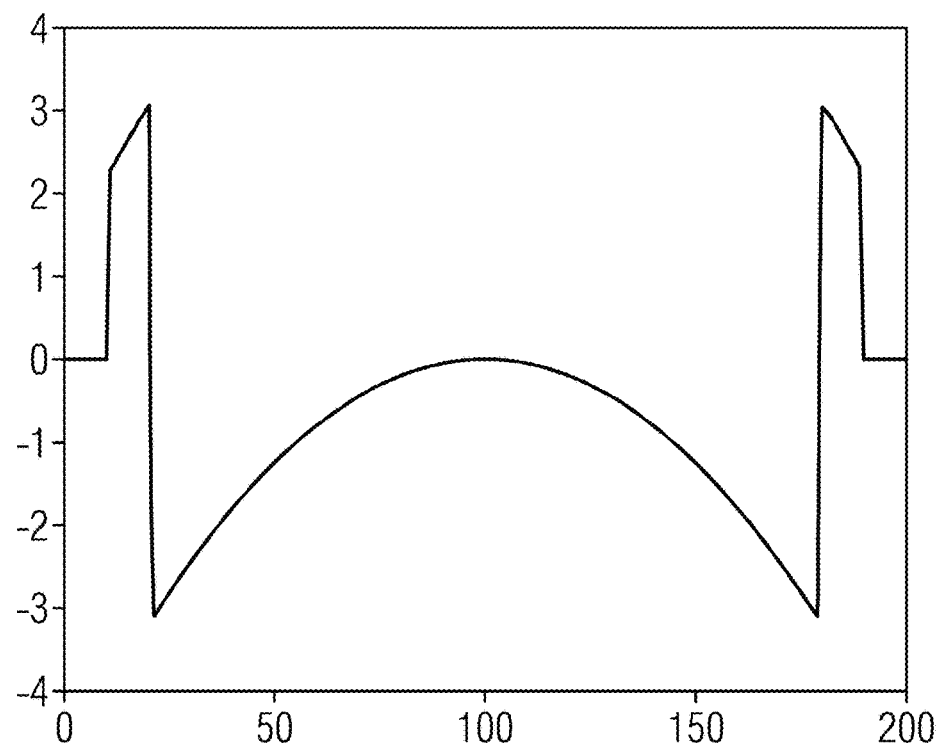

FIG. 6b shows a line graph of the corrected phase-difference distribution shown in FIG. 6a of the region of interest along a central line of the two-dimensional representation in FIG. 6a.

It can be clearly seen that the problem of ambiguous values in the edge region is much less pronounced. As a result, it is possible to assign an absolute phase difference—for example by means of "phase-unwrapping" methods—with a high degree of probability even in the case of noisy data. In order to generate a continuous phase-difference distribution from the corrected phase-difference distribution in FIG. 6 without restriction to the interval $[-\pi; +\pi]$, in a next step a phase-unwrapping technique is applied to the corrected phase-difference distribution. It is also possible to use filter methods to generate a continuous phase-difference distribution, as is known from the prior art. As a result, the object-induced phase difference $\Delta\varphi^*(r)$ is obtained without restriction of the value range, as shown in FIG. 7.

Figure 7:
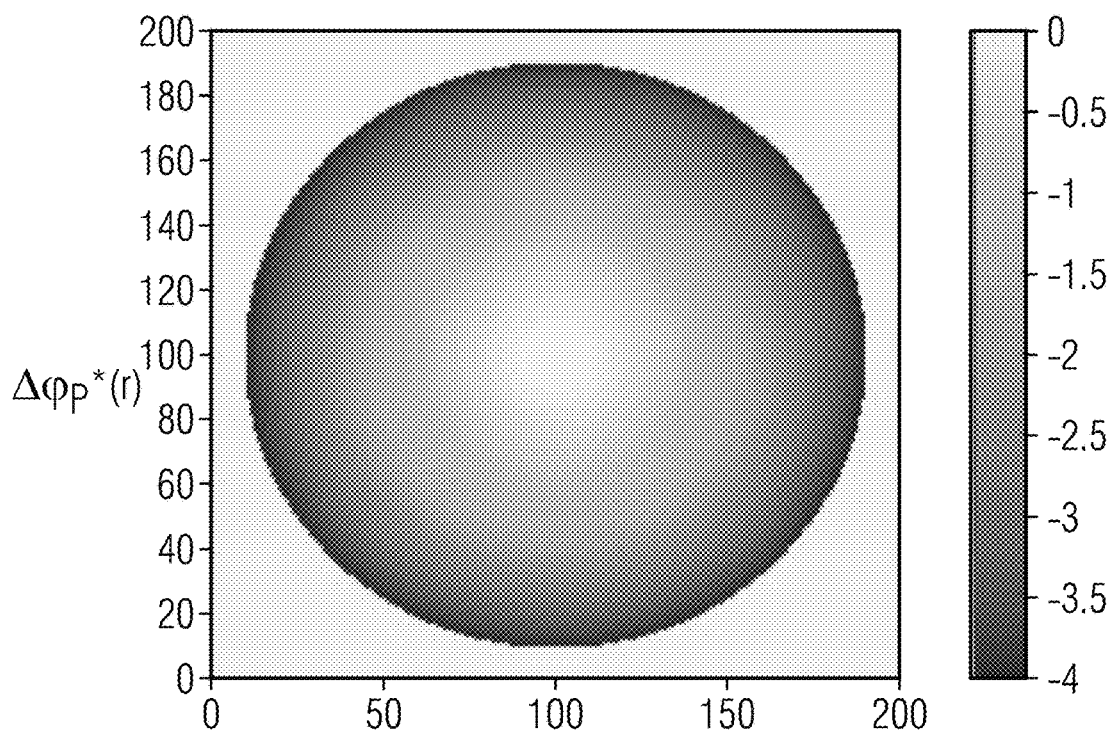
FIG. 7 shows a two-dimensional representation of an absolute phase-difference distribution $\Delta\varphi^*(r)$ of the region of interest, which was generated by a phase-unwrapping technique from the corrected phase-difference distribution in FIG. 6 and wherein the phase values thereof are not restricted to the interval $[-\pi; +\pi]$.

FIG. 7 shows a two-dimensional representation of an absolute phase-difference distribution $\Delta\varphi^*(r)$ of the region of interest, which was generated by a phase-unwrapping technique from the corrected phase-difference distribution in FIG. 6 and wherein the phase values thereof are not restricted to the interval $[-\pi; +\pi]$.

In the last step, the previously separated magnetic component is taken into account once again. Herein, it is essential that the value range of this contribution is not restricted since the absolute value of $B_M(r)$ is known a priori. In this way, the spatial distribution of the absolute phase differences is obtained directly and, derived therefrom, the sought-for spatial B0 distribution as in shown FIG. 8 is obtained from the formula:

$$\Delta\varphi^*(r)=\Delta\varphi^*_P(r)+\gamma\Delta B_M(r)(T_{eff,1}-T_{eff,2})$$

Figure 8:
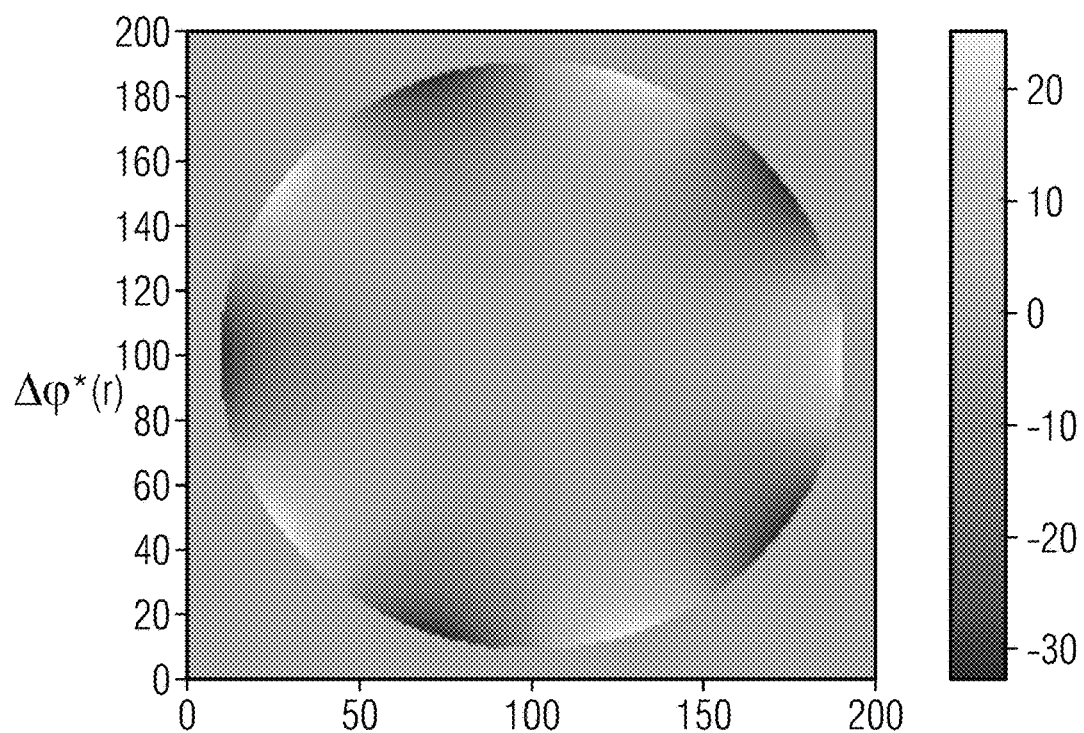
FIG. 8 shows a two-dimensional representation of a spatial magnetic field distribution of the $B_0$ field, which was calculated from the absolute phase-difference distribution in FIG. 7.

FIG. 8 shows a two-dimensional representation of a spatial magnetic field distribution of the $B_0$ field, which was calculated from the absolute phase-difference distribution in FIG. 7.

FIG. 9 is a flowchart with steps for carrying out the method for the determination of a phase distribution of a region of interest according to an exemplary embodiment of the invention.

The method starts in step S40. In step S41, a first measured phase distribution of the region of interest is provided. In step S42, at least one second phase value is provided. In step S43, the first measured phase distribution and the at least one second phase value are combined with one another to generate a combination-phase distribution. Herein, the phase values of the combination-phase distribution are restricted to a defined presentation interval. In step S44, a correction-phase distribution is generated, which is based on the known magnetic field distribution in the region of interest. Herein, the phase values of the correction-phase distribution are not restricted to the defined presentation interval. In step S45, a corrected combination-phase distribution is generated using the correction-phase distribution and the combination-phase distribution, wherein the phase values of the corrected combination-phase distribution are restricted to the defined presentation interval. In step S46, an absolute combination-phase distribution is generated from the corrected combination-phase distribution, wherein the phase values of the absolute combination-phase distribution are not restricted to the defined presentation interval. The method ends in step S47, which includes using said phase values of said absolute combination-phase distribution to reconstruct image data from said MR signals, and using said image data to present a visualization of said region of interest at a display screen.

In an exemplary embodiment, when recording with a number of coil elements, the method according to the invention is first applied to the phase data of each individual element. This is following by a conventional combination taking account of the phase information.

In another exemplary embodiment, first the data from all coil elements is combined in the conventional way taking account of the phase information. This is followed by the application of the method according to the invention to the combination-phase data.

In a further exemplary embodiment, more than two measurements are performed with different effective evolution times, wherein the method according to the invention is applied to any combinations of signal phases.

In an additional exemplary embodiment, when performing more than one measurement with different effective evolution times, the method according to the invention is applied to both the individual measurements (i.e. before the combination of the signal phases) and to the combined measurements.

Due to the improved robustness to the strong magnetic field variations in the edge region, the method according to the invention enables high-precision results even with coarser voxels within the region of interest. This permits, for example, accelerated recording of a large spatial region with reduced resolution, for example for recording B0 maps during adjustment procedures.

In addition to the fixed basic field magnet, further elements can contribute to in local variations of the B0 field (and hence in phase variation). If the influence of these elements on the spatial magnetic field distribution and the position of the elements relative to the basic field magnet are known, these components can also be taken into account during the separation according to the invention. Examples of fixed elements include covering, an RF whole-body coil, gradient coils and shim coils. In the case of gradient coils and shim coils, the variable, known settings of the additional fields generated thereby are taken into account with linear geometry or also higher order geometry. Examples of non-fixed elements with a known position are a patient bench, positioning aids and local RF coils.

In summary, the method for the determination of a phase distribution of a region of interest is carried out. A combination of phase distributions of the region of interest, which were determined in order to generate an MR image of the region of interest by means of an MR system, is performed, wherein a known magnetic field distribution in the region of interest is taken into account. According to the invention a component of a priori known spatial variations of the signal phase of measured data are separated in order to a generate a more benign spatial phase distribution, which is substantially induced by an object.

According to the invention, the method utilizes previous knowledge of a spatial distribution of a basic magnetic field, in particular rapidly spatially varying contributions in an edge region of a region of interest due to system-induced known magnetic field variations, such as, for example, magnetic field variations induced by the design of the basic field magnet and thus reduces errors in the determination of phase differences in the edge region of the region of interest.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for generating magnetic resonance (MR) image data representing a region of interest of an examination subject, said method comprising:
   operating an MR data acquisition scanner in order to obtain a first measured phase distribution of MR signals acquired from said region of interest, wherein the first measured phase distribution of MR signals is based on a magnetic field distribution that is known a priori in absolute values, and is substantially not object-induces;
   providing said first measured phase distribution of the region of interest to a computer and providing said computer with an input designating at least one second phase value of the region of interest;
   in said computer, determining a phase difference distribution between said first measured phase distribution and said at least one second phase value in order to generate a combination-phase distribution, wherein phase values of the combination-phase distribution are restricted to a presentation interval;
   in said computer, calculating a correction-phase distribution, from the known magnetic field distribution in said scanner in said region of interest, wherein phase values of said correction-phase distribution are not restricted to said presentation interval;
   in said computer, generating a corrected combination-phase distribution using the correction-phase distribution and the combination-phase distribution, wherein phase values of the corrected combination-phase distribution are restricted to said presentation interval;
   in said computer, generating an absolute combination-phase distribution from the corrected combination-phase distribution using a phase-unwrapping technique, wherein phase values of the absolute combination-phase distribution are not restricted to said predetermined presentation interval; and
   in said computer, using said phase values of said absolute combination-phase distribution to reconstruct image data from said MR signals, and using said image data to present a visualization of said region of interest at a display screen.

2. A method as claimed in claim 1 comprising generating a corrected absolute combination-phase distribution which is not restricted to said presentation interval, by adding the correction-phase distribution and the absolute combination-phase distribution in order to determine a main magnetic field distribution.

3. A method as claimed in claim 1, comprising determining the correction-phase distribution $\varphi_{korr}(r)$ according to $\varphi_{korr}(r)=\gamma\Delta B_0(r)T_{\mathit{eff}}$, wherein $\gamma$ is the gyromagnetic ratio, $\Delta B_0(r)$ is a magnetic field distribution in the region of interest, which is not object-induced, r is the position vector in the region of interest, and $T_{\mathit{eff}}$ is an effective evolution time.

4. A method as claimed in claim 1 comprising acquiring said first measured phase distribution by measurement of a phase distribution of an MR image of the region of interest after a first evolution period of nuclear spins in the region of interest.

5. A method as claimed in claim 4 comprising providing said at least one second phase value as a second measured phase distribution of the region of interest.

6. A method as claimed in claim 5 comprising providing the second measured phase distribution as a measurement of a phase distribution of an MR image after a second evolution period of said nuclear spins that is different from said first evolution period.

7. A method as claimed in claim 1 comprising providing said at least one second phase value as a definition of a global phase value.

8. A magnetic resonance (MR) apparatus comprising:
   an MR data acquisition scanner;
   a computer configured to operate said MR data acquisition scanner in order to obtain a first measured phase distribution of MR signals acquired a region of interest, wherein the first measured phase distribution of MR signals is based on a magnetic field distribution that is know a priori in absolute values, and is substantially not object-induced;
   said computer being provided with an input designating at least one second phase value of the region of interest;
   said computer being configured to determine a phase difference distribution between first measured phase distribution and said at least one second phase value in order to generate a combination-phase distribution, wherein phase values of the combination-phase distribution are restricted to a presentation interval;
   said computer being configured to calculate a correction-phase distribution, from the known magnetic field distribution in said scanner in said region of interest, wherein phase values of said correction-phase distribution are not restricted to said presentation interval;
   said computer being configured to generate a corrected combination-phase distribution using the correction-phase distribution and the combination-phase distribution, wherein phase values of the corrected combination-phase distribution are restricted to said presentation interval;
   said computer being configured to generate an absolute combination-phase distribution from the corrected combination-phase distribution using a phase-unwrapping techinque, wherein phase values of the absolute combination-phase distribution are not restricted to said presentation interval; and
   said computer being configured to use said phase values of said absolute combination-phase distribution to reconstruct image data from said MR signals, and to use said image data to present a visualization of said region of interest at a display screen.

9. A non-transitory, computer-readable data storage medium encoded with programming instructions, said storage medium being loaded into a computer system of a magnetic resonance (MR) apparatus comprising an MR data acquisition scanner, said programming instructions causing said computer system to:
   operate said MR data acquisition scanner in order to obtain a first measured phase distribution of MR signals acquired from a region of interest, wherein the first measured phase distribution of MR signals is based on a magnetic field distribution that is known a priori in absolute value, and is substantially not object-induced;

receive an input designating at least one second phase value of the region of interest;

determine a phase difference distribution between said first measured phase distribution and said at least one second phase value in order to generate a combination-phase distribution, wherein phase values of the combination-phase distribution are restricted to a presentation interval;

calculate a correction-phase distribution, from the known magnetic field distribution in said scanner in said region of interest, wherein phase values of said correction-phase distribution are not restricted to said presentation interval;

generate a corrected combination-phase distribution using the correction-phase distribution and the combination-phase distribution, wherein phase values of the corrected combination-phase distribution are restricted to said presentation interval;

generate an absolute combination-phase distribution from the corrected combination-phase distribution using a phase-unwrapping technique, wherein phase values of the absolute combination-phase distribution are not restricted to said presentation interval; and use said phase values of said absolute combination-phase distribution to reconstruct image data from said MR signals, and use said image data to present a visualization of said region of interest at a display screen.

* * * * *